United States Patent
Taylor, Jr. et al.

(10) Patent No.: US 7,432,299 B2
(45) Date of Patent: Oct. 7, 2008

(54) METHOD OF TREATMENT FOR SEXUAL DYSFUNCTION

(75) Inventors: Charles Price Taylor, Jr., Chelsea, MI (US); Andrew John Thorpe, Whitmore Lake, MI (US); Pieter Hadewijn Van Der Graaf, Deal (GB); Christopher Peter Wayman, Deal (GB); David Juergen Wustrow, Ann Arbor, MI (US)

(73) Assignee: Pfizer Inc., New York, NY (US)

( * ) Notice: Subject to any disclaimer, the term of this patent is extended or adjusted under 35 U.S.C. 154(b) by 585 days.

(21) Appl. No.: 10/726,878

(22) Filed: Dec. 2, 2003

(65) Prior Publication Data

US 2004/0176456 A1    Sep. 9, 2004

Related U.S. Application Data

(60) Provisional application No. 60/433,491, filed on Dec. 13, 2002.

(51) Int. Cl.
    *A61K 31/195* (2006.01)
(52) U.S. Cl. .................................................. 514/561
(58) Field of Classification Search ............... None
    See application file for complete search history.

(56) References Cited

U.S. PATENT DOCUMENTS

| | | | | |
|---|---|---|---|---|
| 2,503,059 A | 4/1950 | Miescher et al. | .......... | 260/309.6 |
| 2,599,000 A | 6/1952 | Kerwin et al. | ............ | 260/570.7 |
| 3,381,009 A | 4/1968 | Palazzo et al. | .............. | 260/268 |
| 3,511,836 A | 5/1970 | Hess | ........................ | 260/256.4 |
| 3,527,761 A | 9/1970 | Archibald et al. | ........... | 260/293 |
| 3,997,666 A | 12/1976 | Witte et al. | .................. | 424/250 |
| 4,024,175 A | 5/1977 | Satzinger et al. | ......... | 260/468 J |
| 4,026,894 A | 5/1977 | Winn et al. | ........... | 260/256.4 Q |
| 4,188,390 A | 2/1980 | Campbell | ................... | 424/251 |
| 4,252,721 A | 2/1981 | Silvestrini et al. | ........ | 260/243.3 |
| 4,315,007 A | 2/1982 | Manoury | .................... | 424/251 |
| 4,703,063 A | 10/1987 | Imai et al. | .................... | 514/603 |
| 5,563,175 A | 10/1996 | Silverman et al. | ........... | 514/561 |
| 5,945,117 A | 8/1999 | El-Rashidy et al. | ......... | 424/430 |
| 2003/0195251 A1 | 10/2003 | Barta et al. | ................. | 514/561 |

FOREIGN PATENT DOCUMENTS

| | | |
|---|---|---|
| EP | 0641330 | 10/2001 |
| EP | 1178034 | 2/2002 |
| EP | 1201240 | 5/2002 |
| EP | 0934061 | 5/2003 |
| WO | WO 9111172 | 8/1991 |
| WO | WO 9402518 | 2/1994 |
| WO | WO 9729101 | 8/1997 |
| WO | WO 9733858 | 9/1997 |
| WO | WO 9733859 | 9/1997 |
| WO | WO 9817627 | 4/1998 |
| WO | WO 9855148 | 12/1998 |
| WO | WO 9921824 | 5/1999 |
| WO | WO 9930697 | 6/1999 |
| WO | WO 9931057 | 6/1999 |
| WO | WO 9931074 | 6/1999 |
| WO | WO 9931075 | 6/1999 |
| WO | WO 0061135 | 10/2000 |
| WO | WO 0076958 | 12/2000 |
| WO | WO 0128978 | 4/2001 |
| WO | WO 0222568 | 3/2002 |
| WO | WO 0228881 | 4/2002 |
| WO | WO 0230871 | 4/2002 |
| WO | WO 0230881 | 4/2002 |
| WO | WO 0242414 | 5/2002 |
| WO | WO 02/085839 | * 9/2002 |
| WO | WO 02085839 | 10/2002 |
| WO | WO 02100347 | 12/2002 |
| WO | WO 02100392 | 12/2002 |
| WO | WO 03000642 | 1/2003 |
| WO | WO 03082807 | 10/2003 |

OTHER PUBLICATIONS

Gee, et al., "The Novel Anticonvulsant Drug, Gabapentin (Neurontin), Binds to the $\alpha_2\delta$ Subunit of a Calcium Channel", *The Journal of Biological Chemistry* 271(10), pp. 5768-5776 (1996).

Williams, et al., "1-(((7,7-Dimethyl-2(S)-(2(S)-amino-4-(methysulfonyl)butyramido)bicyclo[2.2.1]-heptan-1(S)-yl)methyl)sulfonyl)-4-(2-mtheylphenyl)piperazine (L-368,899): An Orally Bioavailable, Non-Peptide Oxytocin Antagonist with Potential Utility for Managina Preterm Labor", *J. Med. Chem.* 37, pp. 565-571 (1994).

Yonezawa, et al., "Characterization of p-chloroamphetamine-induced penile erection and ejaculation in anesthetized rats", *Life Sciences* 67, pp. 3031-3039 (2000).

Tamkai, et al., "Synthesis of 4-cis-Phenyl-L-proline via Hydrogenolysis", *J. Org. Chem.* 66, pp. 3593-3596 (2001).

*The Merck Manual*, 6th Edition, "Orgasm Disorders", pp. 1576-1577, by Merck Research Laboratories (1992).

Harden, et al., "Treatment of sexual disorders in people with epilepsy", *Epilepsy & Behavior*, vol. 3, pp. S38-S41, (2002).

* cited by examiner

*Primary Examiner*—Raymond J Henley, III
(74) *Attorney, Agent, or Firm*—Gregg C. Benson; John A. Wichtowski

(57) ABSTRACT

Use of an alpha-2-delta ligand, or a pharmaceutically acceptable derivative thereof, for the manufacture of a medicament for the treatment of premature ejaculation.

12 Claims, 1 Drawing Sheet

METHOD OF TREATMENT FOR SEXUAL DYSFUNCTION

This application claims priority from U.S. Provisional Application Ser. No. 60/433,491 filed on Dec. 13, 2002.

This invention relates to a new use of alpha-2-delta ligands and their pharmaceutically acceptable derivatives. In particular it relates to a new use of gabapentin, pregabalin, (1α,3α,5α) (3-amino-methyl-bicyclo[3.2.0]hept-3-yl)-acetic acid and [(1R,5R,6S)-6-(Aminomethyl)bicyclo[3.2.0]hept-6-yl] acetic acid.

Premature ejaculation may be defined as persistent or recurrent ejaculation before, upon or shortly after penile penetration of a sexual partner. It may also be defined as ejaculation occurring before the individual wishes [see 'The Merck Manual', 16$^{th}$ edition, p 1576, published by Merck Research Laboratories, 1992].

Alpha-2-delta ligands have been described for a number of indications. The best known alpha-2-delta ligand, gabapentin (I), known as Neurontin®, 1-(aminomethyl)-cyclohexylacetic acid, was first described in the patent literature in the patent family comprising U.S. Pat. No. 4,024,175.

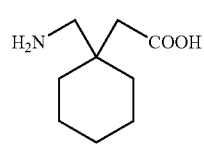

(I)

The compound is approved for the treatment of epilepsy and neuropathic pain.

A second alpha-2-delta ligand, pregabalin (II), (S)-(+)-4-amino-3-(2-methylpropyl)butanoic acid, is described in European patent application publication number EP641330 as an anti-convulsant treatment useful in the treatment of epilepsy and in EP0934061 for the treatment of pain.

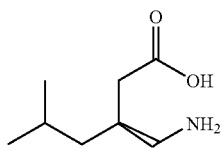

(II)

More recently, Patent Application WO02/085839 describes alpha-2-delta ligands of the following formulae:

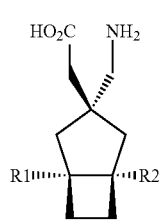

(III)

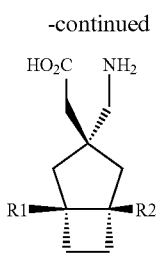

(IV)

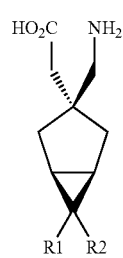

(V)

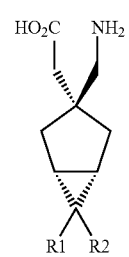

(VI)

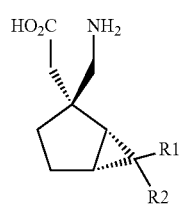

(VII)

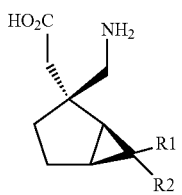

(VIII)

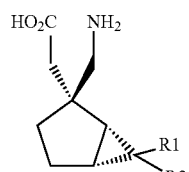

(IX)

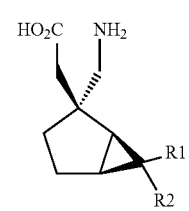

(X)

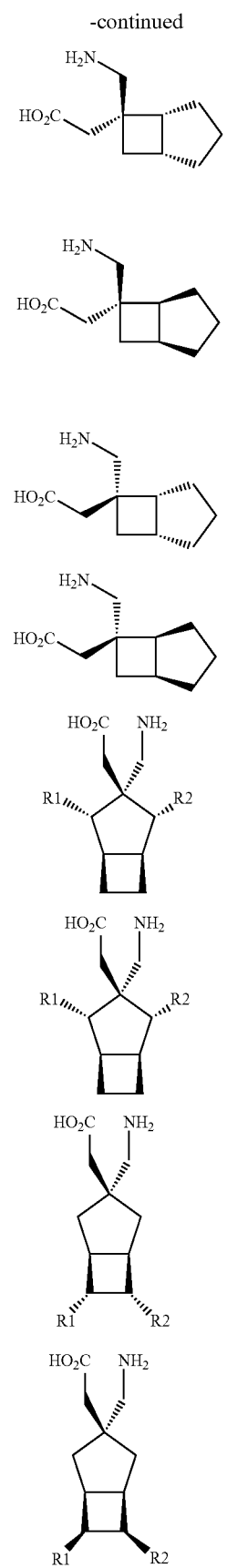
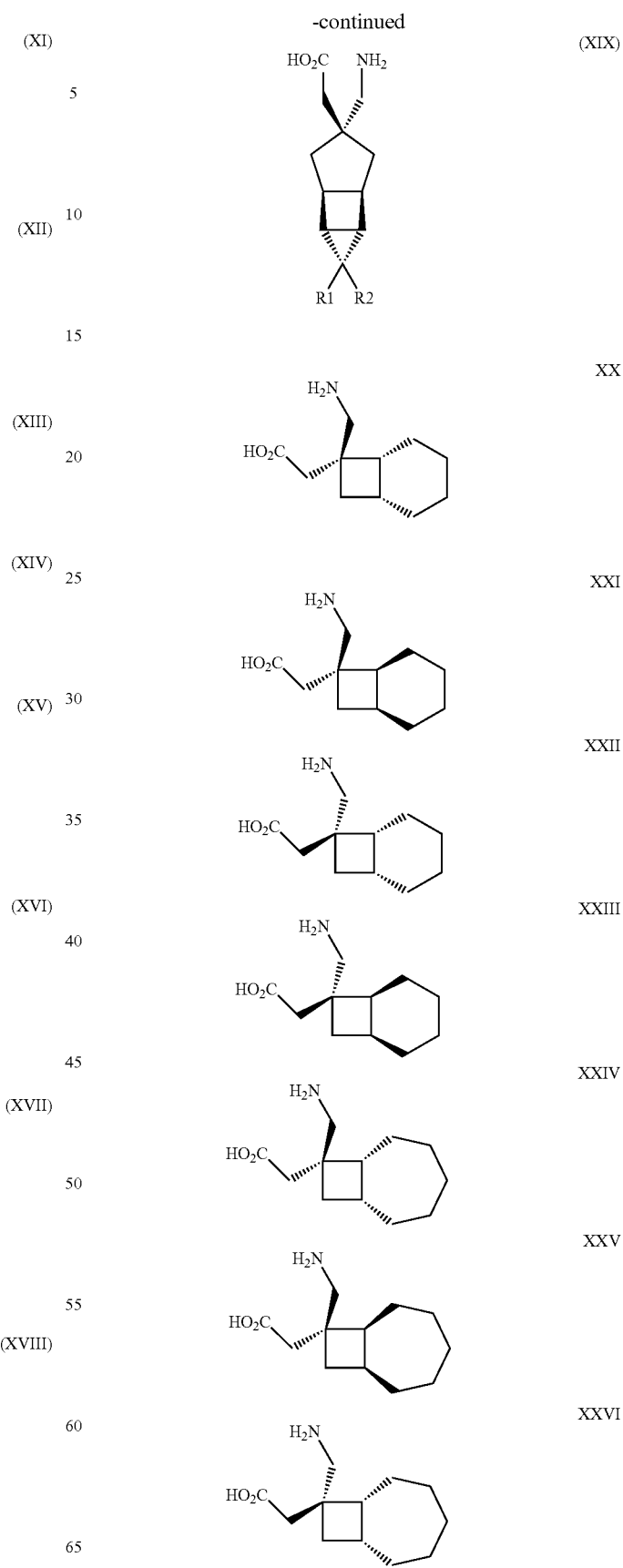

-continued

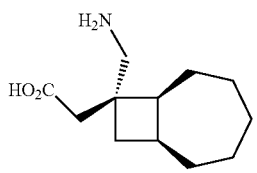
(XXVII)

wherein R¹ and R² are each independently selected from H, straight or branched alkyl of 1-6 carbon atoms, cycloalkyl of from 3-6 carbon atoms, phenyl and benzyl, subject to the proviso that, except in the case of a tricyclooctane compound of formula (XVIII), R¹ and R² are not simultaneously hydrogen; for use in the treatment of a number of indications, including pain.

Further examples of alpha-2-delta ligands are those compounds generally or specifically disclosed in U.S. Pat. Nos. 4,024,175, 5,563,175, WO9733858, WO9733859, WO9931057, WO9931074, WO9729101, WO9931075. Particularly of interest are

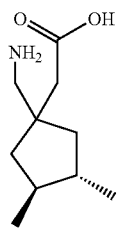
(XXVIII)

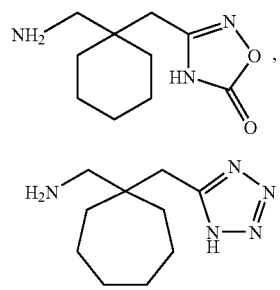
(XXIX)

disclosed in WO9931075; and

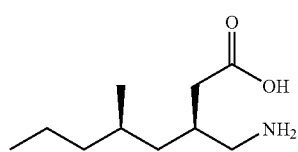
(XXX)

disclosed in WO0076958; and

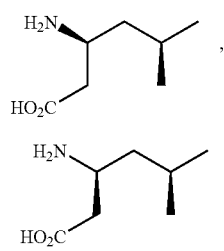
(XXXI)

(XXXII)

disclosed in U.S. Application Ser. No. 60/368413; and

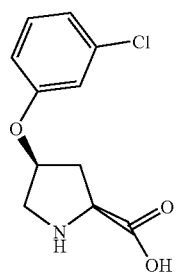
(XXXIII)

WO 00/61135 describes the use of analogs of glutamic acid and gamma-aminobutyric acid as being useful in treating incontinence.

Further examples of alpha-2-delta ligands are the compounds depicted below:

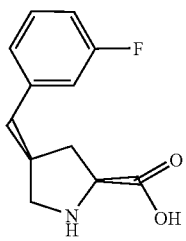
XXXIV

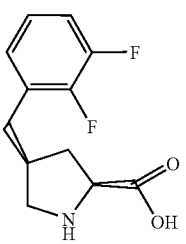
XXXV

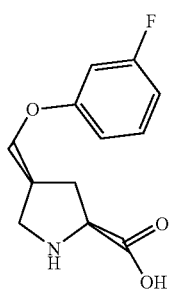
XXXVI

XXXVII

Additional cyclic alpha-2-delta ligands of the present invention are illustrated by the following formula (XXX-VIII):

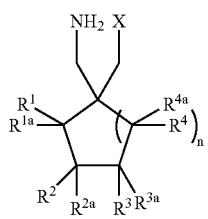

(XXXVIII)

wherein X is a carboxylic acid or carboxylic acid bioisostere; n is 0, 1 or 2; and $R^1$, $R^{1a}$, $R^2$, $R^{2a}$, $R^3$, $R^{3a}$, $R^4$ and $R^{4a}$ are independently selected from H and $C_1$-$C_6$ alkyl, or $R^1$ and $R^2$ or $R^2$ and $R^3$ are taken together to form a $C_3$-$C_7$ cycloalkyl ring, which is optionally substituted with one or two substituents selected from $C_1$-$C_6$ alkyl, or a pharmaceutically acceptable salt thereof.

In formula (XXXVIII), suitably, $R^1$, $R^{1a}$, $R^{2a}$, $R^{3a}$, $R^4$ and $R^{4a}$ are H and $R^2$ and $R^3$ are independently selected from H and methyl, or $R^{1a}$, $R^{2a}$, $R^{3a}$ and $R^{4a}$ are H and $R^1$ and $R^2$ or $R^2$ and $R^3$ are taken together to form a $C_3$-$C_7$ cycloalkyl ring, which is optionally substituted with one or two methyl substituents. A suitable carboxylic acid bioisostere is selected from tetrazolyl and oxadiazolonyl. X is preferably a carboxylic acid.

In formula (XXXVIII), preferably, $R^1$, $R^{1a}$, $R^{2a}$, $R^{3a}$, $R^{4a}$ and $R^{4a}$ are H and $R^2$ and $R^3$ are independently selected from H and methyl, or $R^{1a}$, $R^{2a}$, $R^{3a}$ and $R^{4a}$ are H and $R^1$ and $R^2$ or $R^2$ and $R^3$ are taken together to form a $C_4$-$C_5$ cycloalkyl ring, or, when n is 0, $R^1$, $R^{1a}$, $R^{2a}$, $R^{3a}$, $R^4$ and $R^{4a}$ are H and $R^2$ and $R^3$ form a cyclopentyl ring, or, when n is 1, $R^1$, $R^{1a}$, $R^{2a}$, $R^{3a}$, $R^4$ and $R^{4a}$ are H and $R^2$ and $R^3$ are both methyl or $R^1$, $R^{1a}$, $R^{2a}$, $R^{3a}$, $R^4$ and $R^{4a}$ are H and $R^2$ and $R^3$ form a cyclobutyl ring, or, when n is 2, $R^1$, $R^{1a}$, $R^2$, $R^{2a}$, $R^3$ $R^{3a}$, $R^4$ and $R^{4a}$ are H, or, n is 0, $R^1$, $R^{1a}$, $R^{2a}$, $R^{3a}$, $R^4$ and $R^{4a}$ are H and $R^2$ and $R^3$ form a cyclopentyl ring.

Further acyclic alpha-2-delta ligands of the present invention are illustrated by the following formula (XXXIX):

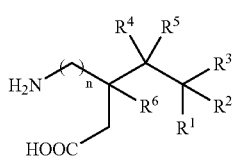

(XXXIX)

wherein:

n is 0 or 1, $R^1$ is hydrogen or $(C_1$-$C_6)$alkyl; $R^2$ is hydrogen or $(C_1$-$C_6)$alkyl; $R^3$ is hydrogen or $(C_1$-$C_6)$alkyl; $R^4$ is hydrogen or $(C_1$-$C_6)$alkyl; $R^5$ is hydrogen or $(C_1$-$C_6)$alkyl and $R^2$ is hydrogen or $(C_1$-$C_6)$alkyl, or a pharmaceutically acceptable salt thereof.

According to formula (XXXIX), suitably $R^1$ is $C_1$-$C_6$ alkyl, $R^2$ is methyl, $R^3$-$R^6$ are hydrogen and n is 0 or 1. More suitably $R^1$ is methyl, ethyl, n-propyl or n-butyl, $R^2$ is methyl, $R^3$-$R^6$ are hydrogen and n is 0 or 1. When $R^2$ is methyl, $R^3$-$R^6$ are hydrogen and n is 0, $R^1$ is suitably ethyl, n-propyl or n-butyl. When $R^2$ is methyl, $R^3$-$R^6$ are hydrogen and n is 1, $R^1$ is suitably methyl or n-propyl. Compounds of formula (II) are suitably in the 3S,5R configuration.

Examples of alpha-2-delta ligands for use with the present invention include those compounds generally or specifically disclosed in U.S. Pat. No. 4,024,175, particularly gabapentin, EP641330, particularly pregabalin, U.S. Pat. No. 5,563,175, WO9733858, WO9733859, WO9931057, WO9931074, WO9729101, WO02085839, particularly [(1R,5R,6S)-6-(Aminomethyl)bicyclo[3.2.0]hept-6-yl]acetic acid, WO9931075, particularly 3-(1-Aminomethyl-cyclohexylmethyl)-4H-[1,2,4]oxadiazol-5-one and C-[1-(1H-Tetrazol-5-ylmethyl)-cycloheptyl]-methylamine, WO9921824, particularly (3S,4S)-(1-Aminomethyl-3,4-dimethyl-cyclopentyl)-acetic acid, WO0190052, WO0128978, particularly (1α,3α, 5α) (3-amino-methyl-bicyclo[3.2.0]hept-3-yl)-acetic acid, EP0641330, WO9817627, WO0076958, particularly (3S, 5R)-3-aminomethyl-5-methyl-octanoic acid, PCT/IB03/00976, particularly (3S,5R)-3-amino-5-methyl-heptanoic acid, (3S,5R) -3-amino-5-methyl-nonanoic acid and (3S,5R)-3-Amino-5-methyl-octanoic acid, EP1178034, EP1201240, WO9931074, WO03000642, WO0222568, WO0230871, WO0230881, WO02100392, WO02100347, WO0242414, WO0232736 and WO0228881 or pharmaceutically acceptable salts thereof, all of which are incorporated herein by reference.

Surprisingly, it has been found that alpha-2-delta ligands, such as those described above, are useful in the treatment of premature ejaculation.

Thus, in accordance with the present invention there is provided the use of an alpha-2-delta ligand for the treatment of premature ejaculation.

In a preferred embodiment the alpha-2-delta ligand is administered on an as needed basis, also known as pro re nata dosing, referred to herein as prn administration.

Suitable alpha-2-delta ligands are those with a binding affinity of less than about 1000 nM Preferred alpha-2-delta ligands are those with a binding affinity of less than about 300 nM More preferred alpha-2-delta ligands are those with a binding affinity of less than about 100 nM.

Most preferred are those alpha-2-delta ligands are those with a binding affinity of less than about 50 nM.

The biological activity of the alpha-2-delta ligands of the invention may be measured in a radioligand binding assay using [$^3$H]gabapentin and the $\alpha_2\delta$ subunit derived from porcine brain tissue (Gee N. S., Brown J. P., Dissanayake V. U. K., Offord J., Thurlow R., Woodruff G. N., *J. Biol. Chem.*, 1996; 271:5879-5776). Results may be expressed in terms of μM or nM α2δ binding affinity.

Preferably the alpha-2-delta-1-ligand is selected from:

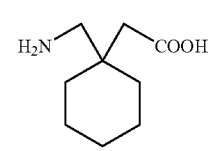

(I)

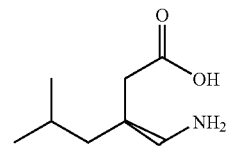

(II)

-continued
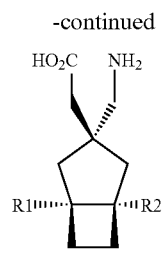
(III)
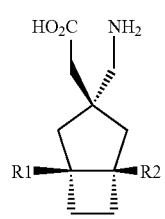
(IV)
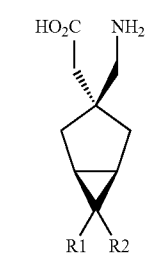
(V)
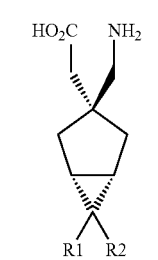
(VI)
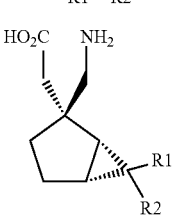
(VII)
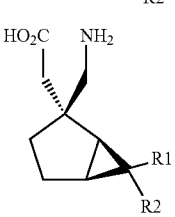
(VIII)
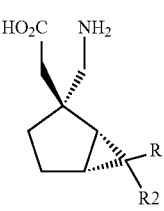
(IX)
-continued
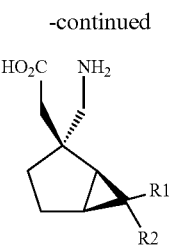
(X)
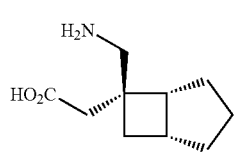
(XI)
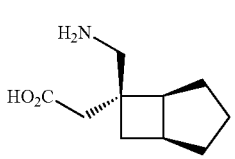
(XII)
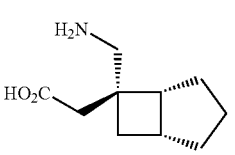
(XIII)
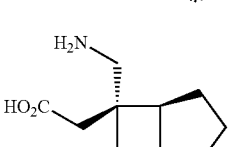
(XIV)
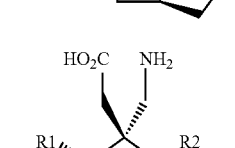
(XV)
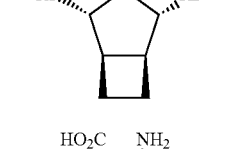
(XVI)
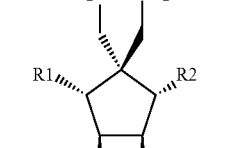
(XVII)
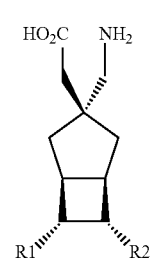

-continued

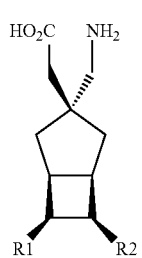
(XVIII)

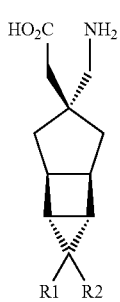
(XIX)

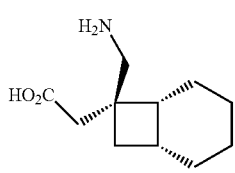
XX

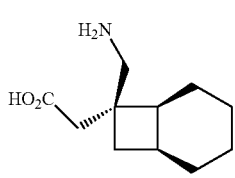
XXI

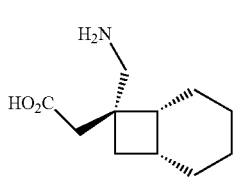
XXII

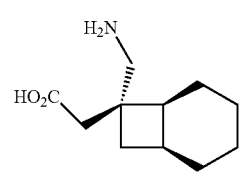
XXIII

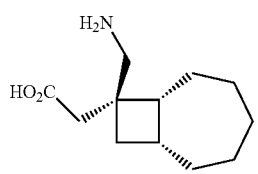
XXIV

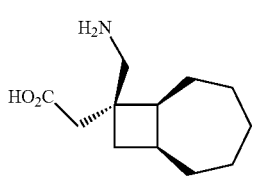
XXV

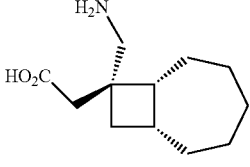
XXVI

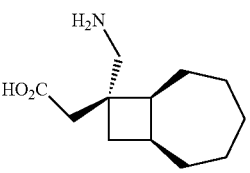
XXVII

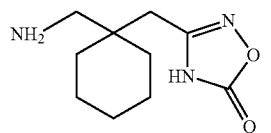
(XXVIII)

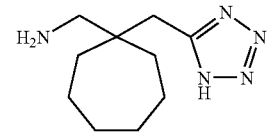
(XXIX)

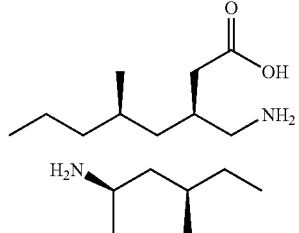
(XXX)

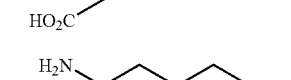
(XXXI)

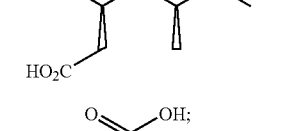
(XXXII)

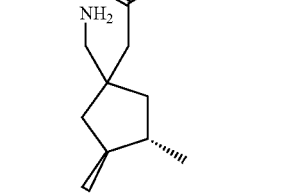
(XXXIII)

or a pharmaceutically acceptable derivative thereof, wherein $R^1$ and $R^2$ are each independently selected from H, straight or branched alkyl of 1-6 carbon atoms, cycloalkyl of from 3-6 carbon atoms, phenyl and benzyl, subject to the proviso that, except in the case of a tricyclooctane compound of formula (XVIII), $R^1$ and $R^2$ are not simultaneously hydrogen;

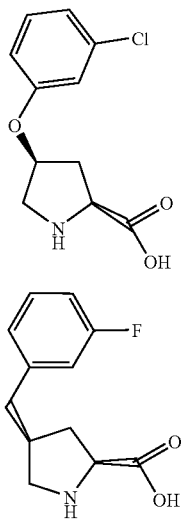

XXXIV

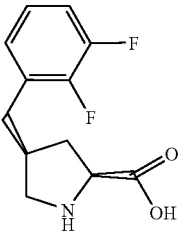

XXXV

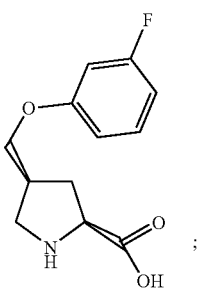

XXXVI

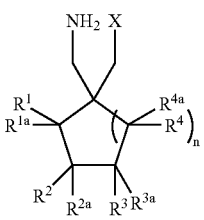

XXXVII compounds of formula (XXXVIII):

(XXXVIII)

wherein X is a carboxylic acid or carboxylic acid bioisostere; n is 0, 1 or 2; and $R^1$, $R^{1a}$, $R^2$, $R^{2a}$, $R^3$, $R^{3a}$, $R^4$ and $R^{4a}$ are independently selected from H and $C_1$-$C_6$ alkyl, or $R^1$ and $R^2$ or $R^2$ and $R^3$ are taken together to form a $C_3$-$C_7$ cycloalkyl ring, which is optionally substituted with one or two substituents selected from $C_1$-$C_6$ alkyl, or a pharmaceutically acceptable salt thereof.

In formula (XXXVIII), suitably, $R^1$, $R^{1a}$, $R^{2a}$, $R^{3a}$, $R^4$ and $R^{4a}$ are H and $R^2$ and $R^3$ are independently selected from H and methyl, or $R^{1a}$, $R^{2a}$, $R^{3a}$ and $R^{4a}$ are H and $R^1$ and $R^2$ or $R^2$ and $R^3$ are taken together to form a $C_3$-$C_7$ cycloalkyl ring, which is optionally substituted with one or two methyl substituents. A suitable carboxylic acid bioisostere is selected from tetrazolyl and oxadiazolonyl. X is preferably a carboxylic acid.

In formula (XXXVIII), preferably, $R^1$, $R^{1a}$, $R^{2a}$, $R^{3a}$, $R^4$ and $R^{4a}$ are H and $R^2$ and $R^3$ are independently selected from H and methyl, or $R^{1a}$, $R^{2a}$, $R^{3a}$ and $R^{4a}$ are H and $R^1$ and $R^2$ or $R^2$ and $R^3$ are taken together to form a $C_4$-$C_5$ cycloalkyl ring, or, when n is 0, $R^1$, $R^{1a}$, $R^{2a}$, $R^{3a}$, $R^4$ and $R^{4a}$ are H and $R^2$ and $R^3$ form a cyclopentyl ring, or, when n is 1, $R^1$, $R^{1a}$, $R^{2a}$, $R^{3a}$, $R^4$ and $R^{4a}$ are H and $R^2$ and $R^3$ are both methyl or $R^1$, $R^{1a}$, $R^{2a}$, $R^{3a}$, $R^4$ and $R^{4a}$ are H and $R^2$ and $R^3$ form a cyclobutyl ring, or, when n is 2, $R^1$, $R^{1a}$, $R^2$, $R^{2a}$, $R^3$, $R^{3a}$, $R^4$ and $R^{4a}$ are H, or, n is 0, $R^1$, $R^{1a}$, $R^{2a}$, $R^{3a}$, $R^4$ and $R^{4a}$ are H and $R^2$ and $R^3$ form a cyclopentyl ring;

Compounds of formula (XXXIX):

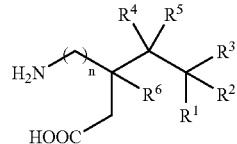

(XXXIX)

wherein:

n is 0 or 1, $R^1$ is hydrogen or $(C_1$-$C_6)$alkyl; $R^2$ is hydrogen or $(C_1$-$C_6)$alkyl; $R^3$ is hydrogen or $(C_1$-$C_6)$alkyl; $R^4$ is hydrogen or $(C_1$-$C_6)$alkyl; $R^5$ is hydrogen or $(C_1$-$C_6)$ alkyl and $R^6$ is hydrogen or $(C_1$-$C_6)$alkyl, or a pharmaceutically acceptable salt thereof.

According to formula (XXXIX), suitably $R^1$ is $C_1$-$C_6$ alkyl, $R^2$ is methyl, $R^3$-$R^6$ are hydrogen and n is 0 or 1. More suitably $R^1$ is methyl, ethyl, n-propyl or n-butyl, $R^2$ is methyl, $R^3$-$R^6$ are hydrogen and n is 0 or 1. When $R^2$ is methyl, $R^3$-$R^6$ are hydrogen and n is 0, $R^1$ is suitably ethyl, n-propyl or n-butyl. When $R^2$ is methyl, $R^3$-$R^6$ are hydrogen and n is 1, $R^1$ is suitably methyl or n-propyl. Compounds of formula (XXXIX) are suitably in the 3S,5R configuration.

Examples of alpha-2-delta ligands for use with the present invention include those compounds generally or specifically disclosed in U.S. Pat. No. 4,024,175, particularly gabapentin, EP641330, particularly pregabalin, U.S. Pat. No. 5,563,175, WO9733858, WO9733859, WO9931057, WO9931074, WO9729101, WO02085839, particularly [(1R,5R,6S)-6-(Aminomethyl)bicyclo[3.2.0]hept-6-yl]acetic acid, WO9931075, particularly 3-(1-Aminomethyl-cyclohexylmethyl)-4H-[1,2,4]oxadiazol-5-one and C-[1-(1H-Tetrazol-5-ylmethyl)-cycloheptyl]-methylamine, WO9921824, particularly (3S,4S)-(1-Aminomethyl-3,4-dimethyl-cyclopentyl)-acetic acid, WO0190052, WO0128978, particularly (1α,3α, 5α) (3-amino-methyl-bicyclo[3.2.0]hept-3-yl)-acetic acid, EP0641330, WO9817627, WO0076958, particularly (3S, 5R)-3-aminomethyl-5-methyl-octanoic acid, PCT/IB03/00976, particularly (3S,5R)-3-amino-5-methyl-heptanoic acid, (3S,5R)-3-amino-5-methyl-nonanoic acid and (3S,5R)-3-Amino-5-methyl-octanoic acid, EP1178034, EP1201240, WO9931074, WO03000642, WO0222568, WO0230871, WO0230881, WO02100392, WO02100347, WO0242414, WO0232736 and WO0228881 or pharmaceutically acceptable salts thereof, all of which are incorporated herein by reference.

More preferably the alpha-2-delta ligand is
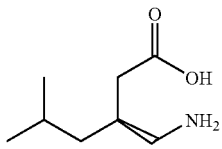 (II)
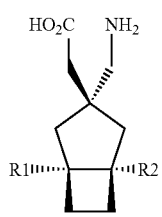 (III)
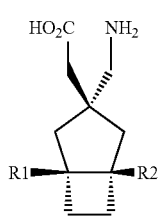 (IV)
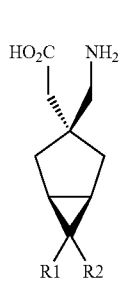 (V)
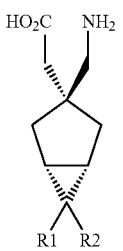 (VI)
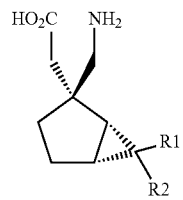 (VII)
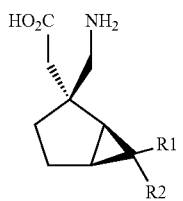 (VIII)
-continued
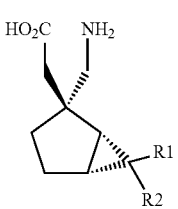 (IX)
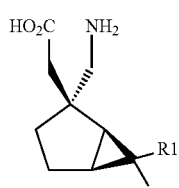 (X)
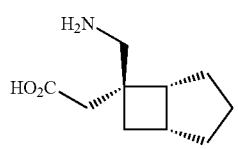 (XI)
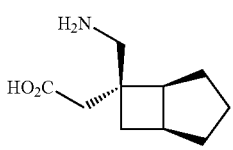 (XII)
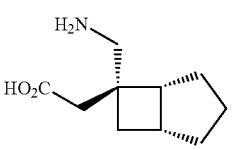 (XIII)
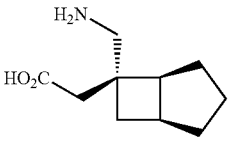 (XIV)
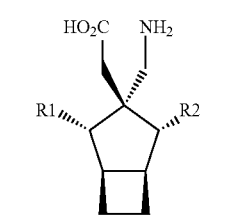 (XV)
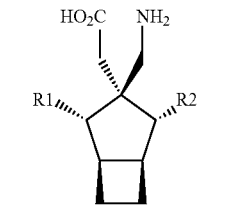 (XVI)

-continued
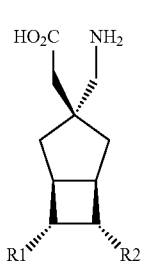
(XVII)
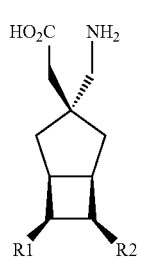
(XVIII)
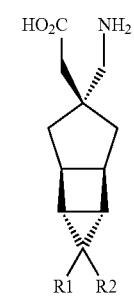
(XIX)
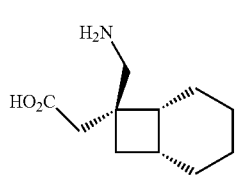
XX
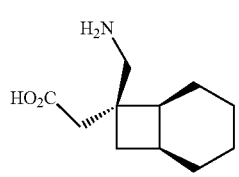
XXI
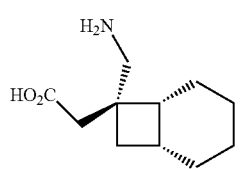
XXII
-continued
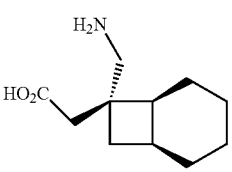
XXIII
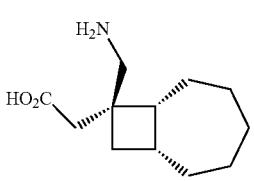
XXIV
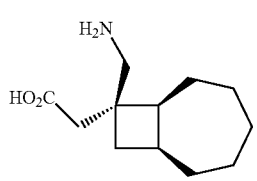
XXV
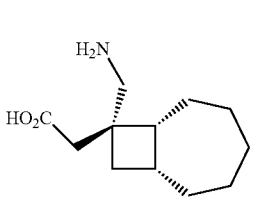
XXVI
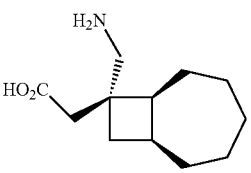
XXVII
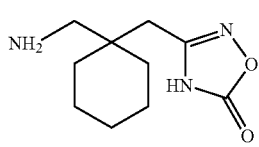
(XXVIII)
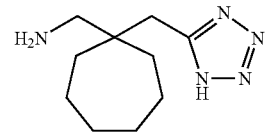
(XXIX)
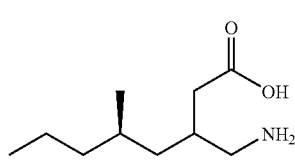
(XXX)

-continued

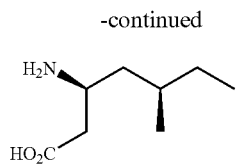
(XXXI)

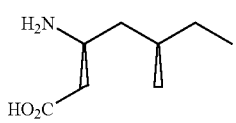
(XXXII)

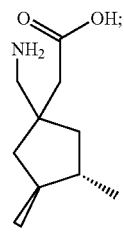
(XXXIII)

or a pharmaceutically acceptable derivative thereof, wherein $R^1$ and $R^2$ are each independently selected from H, straight or branched alkyl of 1-6 carbon atoms, cycloalkyl of from 3-6 carbon atoms, phenyl and benzyl, subject to the proviso that, except in the case of a tricyclooctane compound of formula (XVIII), $R^1$ and $R^2$ are not simultaneously hydrogen; and

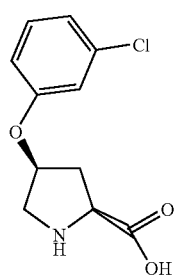
XXXIV

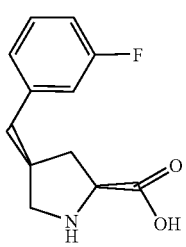
XXXV

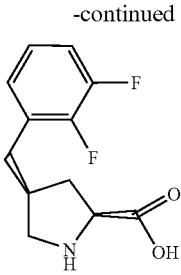
XXXVI

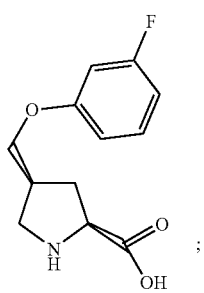
XXXVII compounds of formula (XXXVIII):

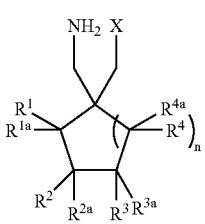
(XXXVIII)

wherein X is a carboxylic acid or carboxylic acid bioisostere; n is 0, 1 or 2; and
$R^1$, $R^{1a}$, $R^{2a}$, $R^{3a}$, $R^4$ and $R^{4a}$ are H and $R^2$ and $R^3$ are independently selected from H and methyl, or $R^{1a}$, $R^{2a}$, $R^{3a}$ and $R^{4a}$ are H and $R^1$ and $R^2$ or $R^2$ and $R^3$ are taken together to form a $C_4$-$C_5$ cycloalkyl ring, or pharmaceutically acceptable salt thereof;
Compounds of formula (XXXIX):

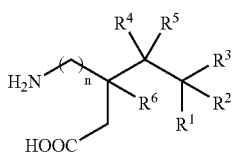
(XXXIX)

wherein:
$R^1$ is methyl, ethyl, n-propyl or n-butyl, $R^2$ is methyl, $R^3$-$R^6$ are hydrogen and n is 0 or 1, or a pharmaceutically acceptable salt thereof. Compounds of formula (XXXIX) are in the 3S,5R configuration.
Yet more preferably the alpha-2-delta ligand is pregabalin (II), (1α,3α,5α)(3-amino-methyl-bicyclo[3.2.0]hept-3-yl)-acetic acid (III')

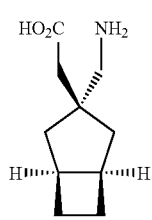

,[(1R,5R,6S)-6-(Aminomethyl)bicyclo[3.2.0]hept-6-yl]acetic acid;

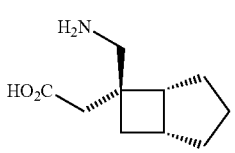

and (2S,4S)-4-(3-Chloro-phenoxy)-pyrrolidine-2-carboxylic acid

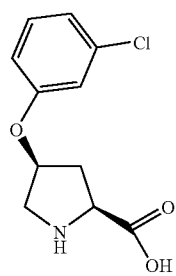

Yet even more preferably the alpha-2-delta ligand is [(1R,5R,6S)-6-(Aminomethyl)bicyclo[3.2.0]hept-6-yl]acetic acid or (2S, 4S)-4-(3-Chloro-phenoxy)-pyrrolidine-2-carboxylic acid.

Most preferably the alpha-2-delta ligand is [(1R,5R,6S)-6-(Aminomethyl)bicyclo[3.2.0]hept-6-yl]acetic acid.

The alpha-2-delta ligand, or pharmaceutically acceptable derivative thereof, can be administered alone or in any convenient pharmaceutical presentation. Oral administration is preferred. In the present indication, a suitable dosage of the alpha-2-delta ligand, or of the active moiety in a pharmaceutically acceptable derivative thereof, is from about 5 to 50 mg/kg of body weight, and preferably about 0.1 to 200 mg/kg. In a more preferred embodiment the dosage is 5 to 15 mg/kg of body weight, most preferably 10 mg/kg of body weight.

The invention further provides a method of treating premature ejaculation comprising administering an alpha-2-delta ligand, or pharmaceutically acceptable derivative thereof, to a patient in need of such treatment.

Alpha-2-delta ligands, particularly the compounds described above, may be used in combination with other compounds. Thus, a further aspect of the present invention is the use of an alpha-2-delta ligand for the manufacture of a medicament in combination with an additional therapeutic agent for the treatment of premature ejaculation. Still further there is provided a product containing an alpha-2-delta ligand and an additional therapeutic agent as a combined preparation for simultaneous, separate or sequential use in the treatment of premature ejaculation.

Suitable additional therapeutic agents include:

Apomorphine—teachings on the use of apomorphine as a pharmaceutical may be found in U.S. Pat. No. 5,945,117;

Dopamine receptor antagonists, particularly dopamine D2, D3 and D4 antagonists such as Premiprixal, Pharmacia Upjohn compound number PNU95666 or levosulphiride;

A serotonin receptor antagonist or modulator, more particularly antagonists or modulators for 5HT1A, including NAD-299 (robalzotan) and WAY-100635, and/or more particularly antagonists or modulators for 5HT3 receptors, including batanopirde, granisetron, ondansetron, tropistron and MDL-73147EF;

A serotonin receptor agonist or modulator, more particularly agonists or modulators for 5HT2C, 5HT1B and/or 5HT1D receptors, including anpirtoline, sumatriptan, eletriptan, frovatriptan, and other triptans well known as anti-migraine medication;

An α-adrenergic receptor antagonist (also known as α-adrenergic blockers, α-blockers or α-receptor blockers); suitable α1-adrenergic receptor antagonists include: phentolamine, prazosin, phentolamine mesylate, trazodone, alfuzosin, indoramin, naftopidil, tamsulosin, phenoxybenzamine, rauwolfa alkaloids, Recordati 15/2739, SNAP 1069, SNAP 5089, RS17053, SL 89.0591, doxazosin, terazosin and abanoquil; suitable α2-adrenergic receptor antagonists include dibenarnine, tolazoline, trimazosin, efaroxan, yohimbine, idazoxan clonidine and dibenarnine; suitable non-selective α-adrenergic receptor antagonists include dapiprazole; further α-adrenergic receptor antagonists are described in WO99/30697, U.S. Pat. Nos. 4,188,390, 4,026,894, 3,511,836, 4,315,007, 3,527,761, 3,997,666, 2,503,059, 4,703,063, 3,381,009, 4,252,721 and 2,599,000 each of which is incorporated herein by reference;

oxytocin receptor antagonists, e.g. L-368 899 (The synthesis of L-368,899 is taught in Williams et al (1994) J. Med. Chem. 37, 565-571).

Vasopressin receptor antagonists

The contents of the published patent applications and in particular the general formulae of the therapeutically active compounds of the claims and exemplified compounds therein are incorporated herein in their entirety by reference thereto.

The use of the compounds and combinations described herein may have the advantage that higher potency, longer duration of action, fewer side effects, improved selectivity, or other more useful properties are achieved compared to the uses of the prior art.

The efficacy of treating premature ejaculation with alpha-2-delta ligands may be demonstrated by use of the anaesthetised rat model of premature ejaculation (Yonezawa et al (2000) Life Sciences 67, 3031-3039)

Alpha-2-delta ligands have been shown to be efficacious in treating premature ejaculation using such a model.

The compounds of the present invention can be administered alone but will generally be administered in admixture with a suitable pharmaceutical excipient, diluent or carrier selected with regard to the intended route of administration and standard pharmaceutical practice.

For example, the compounds of the present invention can be administered orally, buccally or sublingually in the form of tablets, capsules, ovules, elixirs, solutions or suspensions, which may contain flavouring or colouring agents, for immediate-, delayed-, modified-, sustained-, pulsed- or controlled-release applications.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the present invention may be combined with various sweetening or flavouring agents, colouring matter or dyes, with emulsifying and/or suspending agents and with diluents such as water, ethanol, propylene glycol and glycerin, and combinations thereof.

The compounds of the present invention can also be administered parenterally, for example, intravenously, intra-arterially, intraperitoneally, intrathecally, intraventricularly, intraurethrally, intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

The compounds of the present invention can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the therapeutic agents and a suitable powder base such as lactose or starch.

Alternatively, the compounds of the present invention can be administered in the form of a suppository or pessary, or they may be applied topically in the form of a gel, hydrogel, lotion, solution, cream, ointment or dusting powder. The compounds of the present invention may also be dermally or transdermally administered, for example, by the use of a skin patch. They may also be administered by the pulmonary or rectal routes.

For application topically to the skin, the compounds of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the present invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

Suitable alpha-2-delta ligand compounds of the present invention may be prepared as described herein below or in the aforementioned patent literature references.

EXAMPLE 1

(2S,4S)-4-(3-Chloro-phenoxy)-pyrrolidine-2-carboxylic acid

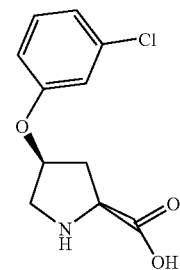

A solution of preparation 2 (29.25 mol) was dissolved in THF (20L) & filtered. To this solution was added 4M HCl in dioxane (30L) & stirred overnight. Tert-Butyl methyl ether (70L) was added to the resultant suspension & the product was collected by filtration (7.06 kg, 86.7%).

$^1$H NMR (400 MHz,CD$_3$OD): δ=2.65 (m,2H), 3.60 (dd, 1H), 3.70 (d, 1H), 4.60 (dd, 1H), 5.02 (m, 1H), 6.88 (m, 1H), 6.97 (s, 1H), 7.03 (d, 1H), 7.29 (dd, 1H). LRMS (Electrospray [MH$^+$]242, [M-1]240. Microanalysis: Found, C, 46.97; H, 4.70; N, 4.90. C$_{11}$H$_{12}$ClNO$_3$.HCl.0.1H$_2$O requires C, 47.20; H, 4.75; N, 5.00.

EXAMPLE 2

(2S,4S)-4-(3-Fluoro-benzyl)-pyrrolidine-2-carboxylic acid mono hydrochloride salt

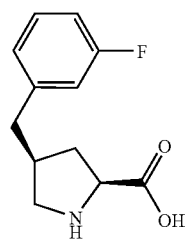

4-(3-Fluoro-benzyl)-pyrrolidine-1,2-dicarboxylic acid 1-tert-butyl ester 2-(2-isopropyl-5-methyl-cyclohexyl) ester (Preparation 3, 0.91 g, 1.96 mmol) was dissolved in toluene (2 ml). 6N hydrochloric acid (50 ml) was added and stirred at reflux for 18 h. The reaction mixture was cooled to room temperature and extracted with ethyl acetate (3×20 ml). The aqueous layer was concentrated by evaporated under reduced pressure to give the title compound (417 mg, 81%) as a white solid. $^1$H-NMR showed a 7:1 ratio of cis:trans diastereoisomers so the product was recrystallised from isopropyl alcohol to give the title compound (170 mg, 65%) in a ratio of 14:1 cis:trans as determined by NMR.

$^1$H-NMR (400 MHz, CD$_3$OD): (mixture of diastereoisomers 2S,4S:2S,4R (14:1)): δ=1.85 (q, 1H), 2.51 (quin, 1H), 2.69-2.85 (m, 3H), 3.07 (t, 1H), 3.41 (dd, 1H), 4.38 and 4.48 (t, 1H), 6.90-7.04 (m, 3H), 7.32 (q, 1H). LRMS (APCI): m/z [MH]$^+$224. $[α]_D^{25}$-1.27° (c=9.00 in methanol). Microanalysis: Found C, 55.56; H, 5.81; N, 5.34%. C$_{12}$H$_{14}$FNO$_2$.HCl requires C, 55.50; H, 5.82; N, 5.39%.

EXAMPLE 3

(2S,4S)-4-(2,3-Difluoro-benzyl)-pyrrolidine-2-carboxylic acid mono-hydrochloride salt

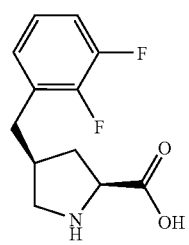

The title compound was made from by the method of Example 2, starting from the title compound of Preparation 4, and purified by re-crystallisation with acetone/ether to give the title compound as a mixture of diastereoisomers (2S,4S: 2S,4R (12:1)) determined by $^1$H-NMR (500 mg, 60%) as a white solid.

$^1$H-NMR (400 MHz, CD$_3$OD) (mixture of diastereoisomers cis:trans (12:1)): δ=0.80-1.90 (m, 0.92H), 2.12-2.20 (m, 0.08H), 2.28-2.36 (m, 0.08H), 2.49-2.58 (q, 0.92H), 2.66-2.81 (m, 1H), 2.83-2.95 (m, 2H), 3.02-3.13 (t, 1H), 3.46 (dd,1H), 4.40 (dd, 0.92H 4.48-4.54 (m, 0.08H), 7.03-7.20 (m, 3H). LRMS (Electrospray): m/z [M+H]$^+$0242. Microanalysis: Found C, 51.42; H, 5.08; N, 5.01%. C$_{12}$H$_{13}$NO$_2$F$_2$.HCl requires C, 51.90; H, 5.08; N, 5.04%.

Example 4

(2S,4S)-4-(3-fluoro-phenoxymethyl)-pyrrolidine-2-carboxylic acid

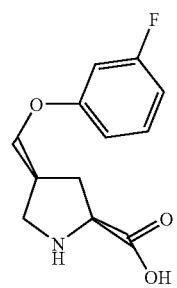

4-(3-fluoro-phenoxymethyl)-pyrroline-1,2-dicarboxylic acid di-tert-butyl ester (Preparation 5, 475 mg, 1.2 mmol) was dissolved in a solution of anhydrous hydrogen chloride in dioxane (4M, 15 ml) and stirred at 50° C. under a nitrogen atmosphere for 1 hour. The solvent was removed under reduced pressure and the resulting semi-solid triturated with ethyl acetate to give a white solid which was recrystallised from ethyl acetate/isopropyl alcohol to give the title compound as a mixture of diastereomers (~5:1 2S,4S:2S,4R) as a white solid hydrochloride salt (90 mg, 35%)

$^1$H-NMR (400 MHz, CD$_3$OD): δ=2.04-2.09 (m, 0.8H); 2.33-2.47 (m, 0.4H); 2.65-2.75 (m, 0.8H); 2.88-3.00 (m, 1H); 3.33-3.40 (m, 1H); 3.52-3.60 (m, 0.8H); 3.60-3.68 (0.2H); 3.96-4.04 (m, 1H); 4.04-4.12 (m, 1H); 4.42-4.51 (m, 0.8H); 4.40-4.56 (m, 0.2H); 6.65-6.80 (m, 3H); 7.21-7.30 (m, 1H)

LRMS (electrospray): [M+1] 240; [M+23] 262; [M−1] 238.

Preparation 1

(2S,4S)-4-(3-Chloro-phenoxy)-pyrrolidine-1,2-dicarboxylic acid 1-tert-butyl ester 2-methyl ester

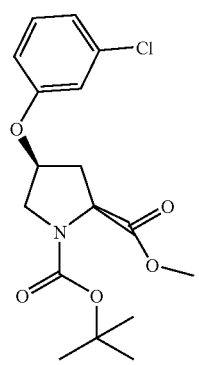

To a stirred solution of (2S,4R)-4-hydroxy-pyrrolidine-1, 2-dicarboxylic acid 1-tert-butyl ester 2-methyl ester (CAS Reg 74844-91-0) (6.1 kg, 24.87 mol), 3-chlorophenol (3.52 kg, 27.39 mol) & triphenylphosphine (7.18 kg, 27.37 mol) in tert-butyl methyl ether (30.5L) at 0'C. was added diisopropylazodicarboxylate (5.53 kg, 27.35 mol) in tert-butyl methyl ether (15L) dropwise. The mixture was stirred overnight at 20'C. The reaction was filtered and the liquors washed with 0.5M sodium hydroxide (aq) (2×12.5L) & water (12.2L). The tert-butyl methyl ether solvent was replaced with n-heptane (42.7L) by atmospheric pressure distillation & cooled to crystallise crude product, which was collected by filtration (11.1 kg, 125% contaminated with ca 35% reduced diisopropyl dicarboxylate & triphenylphosphine oxide-corrected yield=86%).

$^1$H NMR (400 MHz, CDCl$_3$): δ=1.46, 1.49 (2×s, 9H), 2.47 (2H, m), 3.71 (5H, m), 4.42 (1H, m), 4.42, 4.54 (1H, 2×m), 4.87 (1H, m), 6.68 (1H, m), 6.79 (1H, s), 6.92 (1H, m), 7.18 (1H, m). LRMS (Electrospray): m/z 378 (MNa$^+$).

Preparation 2

(2S,4S)-4-(3-Chloro-phenoxy)-pyrrolidine-1,2-dicarboxylic acid 1-tert-butyl ester

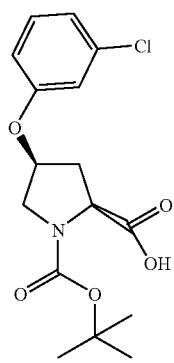

To the products of preparation 1 (11.1 kg, 20.28 mol) in THF (26.6L) was added a solution of LiOH.H$_2$O (4.86 kg, 115.4 mol) in water (55.5L). The mixture was stirred overnight at 25'C. The THF was removed by distillation & the resultant aqueous solution extracted with dichloromethane (33.3L & 16.7L). The combined dichloromethane layers were extracted with water (33L & 16.7L). The combined aqueous phases were adjusted to pH 3-3.5 with 1M hydrochloric acid (aq) & extracted with dichloromethane (2×22.2L). The combined dichloromethane phases were replaced with toluene (33.3L), which was cooled to crystallise the product, which was collected by filtration (6.1 kg, 98%).

$^1$H NMR (400 MHz, CDCl$_3$): δ=1.42, 1.48 (2×s, 9H), 2.30-2.70 (m, 2H), 3.60-3.80 (m, 2H), 4.40-4.60 (m, 1H), 4.86 (m, 1H), 6.71 (m, 1H), 6.82 (m, 1H), 6.94 (m, 1H), 7.16 (m, 1H). LRMS (Electrospray): m/z [MNa+] 364, 340 [M−1] 340.

Preparation 3

4-(3-Fluoro-benzyl)-pyrrolidine-1,2-dicarboxylic acid 1-tert-butyl ester 2-(2-isopropyl-5-methyl-cyclohexyl) ester

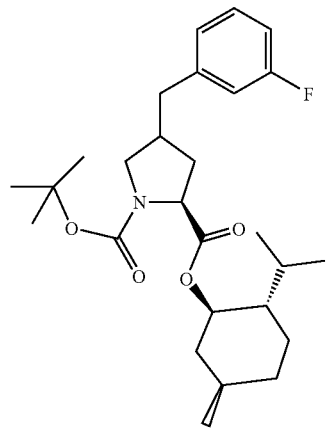

4-(3-Fluoro-benzylidene)-pyrrolidine-1,2-dicarboxylic acid 1-tert-butyl ester 2-(2-isopropyl-5-methyl-cyclohexyl) ester (1.20 g, 2.61 mmol) was dissolved in ethyl acetate:toluene (1:1, 12 ml). The solution was submitted to hydrogenation on platinum oxide (120 mg, 10% by weight) at 25 ° C. and 15 psi for 1 hour. The reaction mixture was filtered through arbocel and the filtrate reduced under pressure. The residue was purified by flashmaster chromatography eluting with heptane:ethyl actetate (15:1) to yield the title compound as a colourless oil (1.11 g, 91%).

$^1$H-NMR (400 MHz, CD$_3$OD): δ=0.72-1.37 (m, 13H), 1.44 (d, 9H), 1.43-1.75 (m, 4H), 1.87-2.01 (m, 2H), 2.31-2.58 (m, 2H), 2.83 (d, 2H), 3.07 (t, 1H), 3.50-3.65 (m, 1H), 4.13-4.30 (dt, 1H), 4.71 (td, 1H), 6.90 (d, 2H), 7.00 (d, 1H), 7.30 (q, 1H).

LRMS (APCl): m/z [MH-BOC]$^+$ 362.

Preparation 4

4-(3-Fluoro-benzyl)-pyrrolidine-1,2-dicarboxylic acid 1-tert-butyl ester 2-(2-isopropyl-5-methyl-cyclohexyl) ester

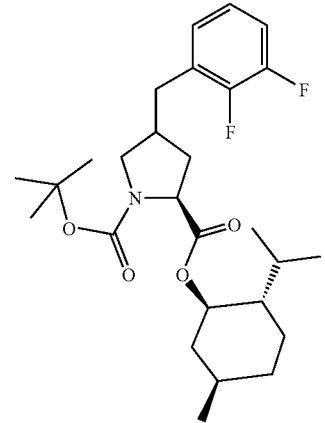

was prepared by a method analogous to that of Preparation 3 using the appropriate starting alkenic menthol ester; [MH]480

Microanalysis (mixture of diastereoisomers cis (major) and trans): Found: C, 67.74; H, 8.30; N, 2.90%. C$_{27}$H$_{39}$F$_2$NO$_4$. requires C, 67.62; H, 8.20; N, 2.92%; [α]$_D^{25}$ −71.92° (c=3.26 in methanol)

Preparation 5

(2S,4S)-Pyrrolidine-1,2,4-tricarboxylic acid 1,2-di-tert-butyl ester

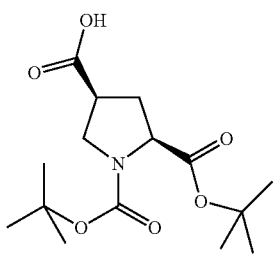

To a mixture of 4-phenyl-pyrrolidine-1,2-dicarboxylic acid di-tert-butyl ester (CAS Reg. No. 344 286-69-7)[5] (0.78 g, 2.24 mmol) and sodium periodate (5.77 g, 27 mmol) stirring at 0° C. under a nitrogen atmosphere in ethyl acetate (5.5 ml), acetonitrile (5.5 ml) and water (8.5 ml) was added ruthenium trichloride (10 mg, 0.05 mmol) and stirred to room temperature over 18 hours. Diethyl ether (20 ml) was added and stirred for a further 1 hr. 1M hydrochloric acid (5 ml) was added and the mixture extracted with ethyl acetate (3×30 ml). Organic extracts were combined, dried ($MgSO_4$), filtered and evaporated under reduced pressure. The residue was purified by chromatography on silica gel, eluting with 50:50:1 ethyl acetate:heptane:glacial acetic acid to give the title compound as a colourless gum (501 mg, 78%)

$^1$H-NMR (400 MHz, $CDCl_3$): δ=1.40-1.49 (m, 18H); 2.26-2.40 (m, 1H); 2.42-2.56 (m, 1H); 3.02-3.12 (m, 1H); 3.65-3.80 (m, 1.4H) & 3.80-3.88 (m, 0.6H) [rotamers]; 4.09-4.20 (m, 0.7H) & 4.20-4.26 (m, 0.3H) [rotamers]LRMS (electrospray): [M−1] 314

[5] J. Org. Chem., 2001, 3593-3596

Biological Data

EXAMPLE 1

Alpha-2-delta Ligands Delay Ejaculation in Anaesthetised Rat Model of Premature Ejaculation In order to study penile erection and ejaculation the method used was based on the methodology taught in Yonezawa et al (2000) Life Sciences 67, 3031-3039. For ease of reference, this methodology is described below:

Male Sprague Dawley rats, weighing 350-450 g, are used. Prior to the experiments the animals are housed in groups (2 rats per cage) under controlled 12 h light-dark cycle (lights on at 07:00), constant temperature (23±1° C.) and humidity (55±5%). They have free access to standard food pellets and water.

Rats are anesthestised with sodium pentobarbitone (50 mg/kg, i.p.) and are placed in the supine position. The penis is extruded from its sheath and gently held by a wooden applicator positioned at the base of the penis. The test compounds are administered orally and p-chloroamphetamine (PCA) (5-10 mg/kg) is administered i.p. immediately before the sheath retraction and the penile responses, including penile erection, redding and expansion of the penile body, glans erection, engorgement and slight flaring of the glans and cup, glans erection with intense flaring of the glans, are recorded in the presence of test compound or vehicle. Latencies from PCA administration to the initial penile response and ejaculation is also measured in seconds in the presence of test compound or vehicle.

The effect of a test compound on p-chloroamphetamine (PCA) induced ejaculation is also assessed by weighing the ejaculates accumulated over 30 mins. A suitable method using conscious rats is described in Renyi (1985) Neuropharmacology, Vol. 24. No. 8, pp 697-704.

Intracavernosal pressure may also be determined in rats anesthetised with sodium pentobarbitone (50 mg/kg, i.p.). The penis is extruded from its sheath and the intracavernosal pressuer (ICP) was measured by inserting a stainless steel needle (23-guauge) into one corpus cavernosum. The needle is attached to a heparinized saline (10 U/ml)-filled teflon tube and connected to a pressure transducer (NEC-San-Ei 7500).

For all the sexual behavour tests, the rapid ejaculating male rats were used as an animal model of premature ejaculation (classified as ejaculatory latency <300 s during baseline assessment). Rapid ejaculating rats were placed in an observation arena (50-60 cm diameter), starting 5 hours into the dark cycle and observed under red ilumination. Three to four minutes after placing the male in the arena, a receptive female (ovariectomised, oestradiol benzoate/progesterone injection 48 hour before behavioural study) was introduced into the arena and the following parameters noted:
i) ejaculatory latency (EJL; time taken from addition of receptive female into the arena to ejaculation);
ii) copulatory efficiency (CE; ejaculatory latency/the number of intromissions to ejaculation, i.e. the number of seconds between intromissions);
iii) intromission frequency (IF; the number of intromissions to ejaculation);
iv) mount frequency (MF; the number of mounts to ejaculation);
v) post ejaculatory interval (PEI; the time taken from ejaculation to the commencement of copulatory behaviour).

The Compound Used in the Following Examples was as Follows:

(1R,5R,6S)-[6-(Aminomethyl)bicyclo[3.2.0]hept-6-yl]acetic acid

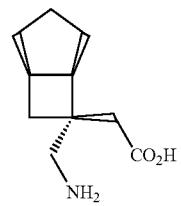

(XI)

EXAMPLE 1a

Figure 1:
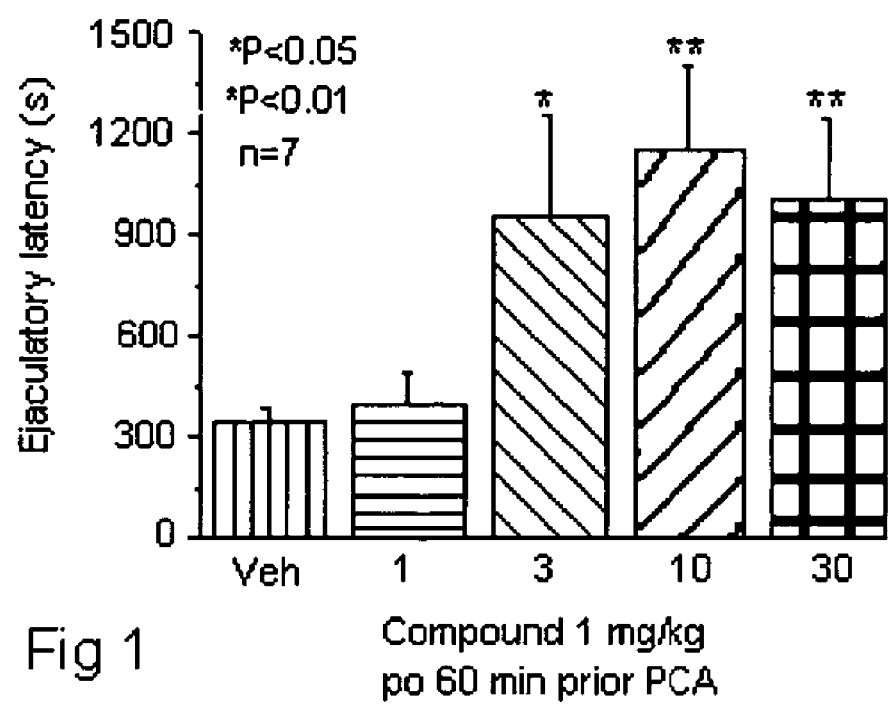
FIG. 1 shows the dosage response results 60 minutes prior to the administration of PCA.

Delayed Ejaculation in the Presence of an Alpha-2-delta Ligand (Compound (XI))

An alpha-2-delta ligand, compound (XI), significantly delayed p-chloroamphetamine (PCA)-induced ejaculation in anaesthetised rats. Compound (XI) was dosed orally and was tested at 1, 3, 10 or 30 mg/kg po, 60 min prior to PCA administration). Compound 1 dose-dependently increased ejaculatory latency by up to 250%. Vehicle treated animals ejaculated in circa 300 s, whereas animals treated Compound 1 at doses above 3 mg/kg po, displayed significantly increased ejaculatory latency to circa 1000 s (See FIG. 1). In this study, at both 3 and 10 mg/kg, 3 out of 7 animals failed to ejaculate within 30 minutes, these animals were assigned ejaculatory latency of 1800 s ie the end of the study in order that a mean delay could be calculated. The quality of erection was not influenced by Compound (XI)—although at 10 and 30 mg/kg a small delay in the time taken to achieve erection was observed.

Using a rodent model of ejaculatory, that reflects human ejaculatory physiology, we have shown that that alpha-2-delta ligands delay ejaculation. Moreover, the study shows that a alpha-2-delta ligands will be useful in the treatment of premature ejaculation by delaying ejaculation.

EXAMPLE 1b

Effect of an Alpha-2-delta Ligand (Compound XI) on Copulatory Behaviour in Rapid Ejaculating Rats Rodent copulatory behaviour is characterised by a series of mounts, with and without vaginal insertion (50-80% of mounts result in intromission [vaginal penetration]) and ejaculation occurs after 6 to 12 intromissions. Each intromission lasts a matter of seconds—it is not possible to quantify intromission length i.e. intravaginal latency. The effect of Compound (XI) was assessed on a number of copulatory parameters (see above). We have focused ejaculatory latency as a clinical biomarker of time taken to achieve ejaculation. The study was performed in rapid ejaculating rats as a model of premature ejaculation (rats characterised by ejaculatory latency <300 s at baseline).

Compound (XI), an alpha-2-delta ligand, increased ejaculatory latency by 58% in rapidly-ejaculating conscious rats (P<0.01); i.e. Compound (XI) (10 mg/kg, 60 min post oral dosing)-treated animals took 219 s to ejaculate compared to 139 s in vehicle treated animals (see Table 2 below). There were no other significant effects of on copulatory behaviour.

TABLE 2

|  | Vehicle | Compound 1 10 mg/kg po |
|---|---|---|
| Ejaculatory latency (sec) | 139 +/− 21 | 219 +/− 26 P < 0.01 | mean ± sem (n = 6).

Using a conscious rapid-ejaculating rodent model of premature ejaculation, that reflects human premature ejaculation pathophysiology, we have shown that an alpha-2-delta ligand will be useful in the treatment of premature ejaculation by delaying ejaculation.

The invention claimed is:

1. A method of treating premature ejaculation comprising administering a therapeutically effective amount of an alpha-2-delta ligand, or a pharmaceutically acceptable salt thereof, to a patient in need of such treatment.

2. The method according to claim 1 wherein administration is on an as needed basis.

3. The method according to claim 1 where the alpha-2-delta ligand is selected from the group:

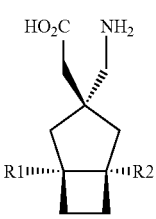

(III)

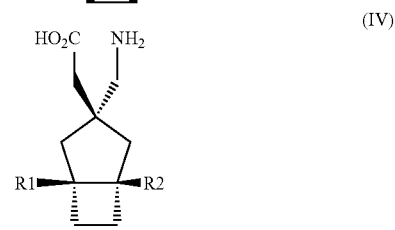

(IV)

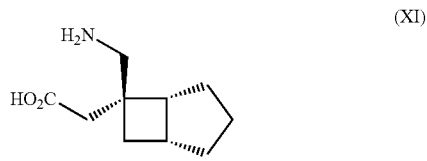

(XI)

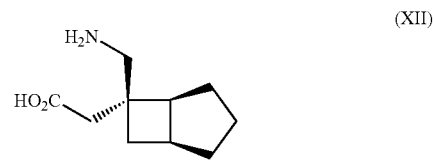

(XII)

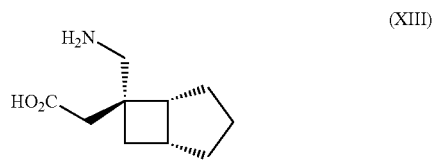

(XIII)

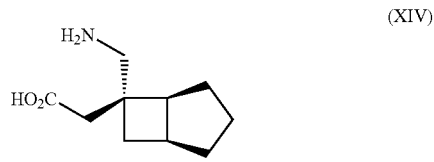

(XIV)

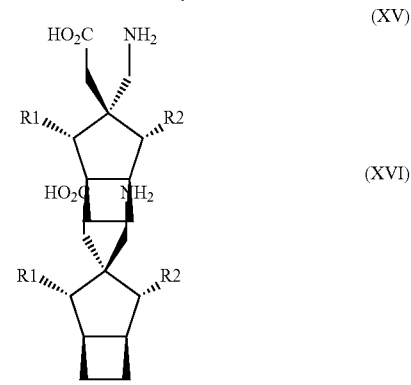

(XV)

(XVI)

-continued

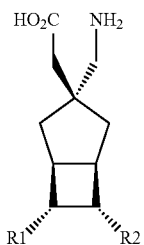
(XVII)

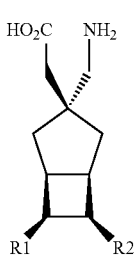
(XVIII)

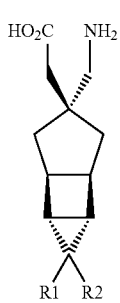
(XIX)

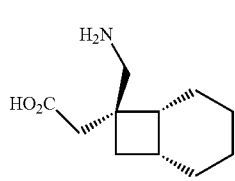
XX

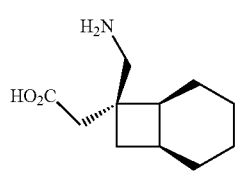
XXI

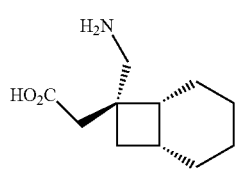
XXII

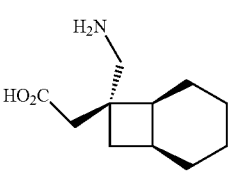
XXIII

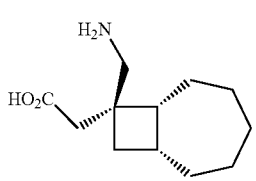
XXIV

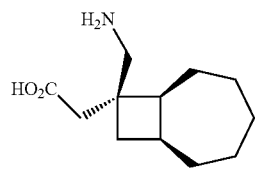
XXV

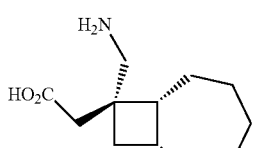
XXVI

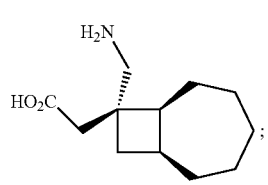
XXVII

;

or a pharmaceutically acceptable salt thereof, wherein $R^1$ and $R^2$ are each independently selected from the group H, straight or branched alkyl of 1-6 carbon atoms, cycloalkyl of from 3-6 carbon atoms, phenyl and benzyl, subject to the proviso that, except in the case of a tricyclooctane compound of formula (XIX), $R^1$ and $R^2$ are not simultaneously hydrogen.

4. The method according to claim 1 where the alpha-2-delta ligand is selected from the group:

(XI)

(XII)

(XIII)

-continued

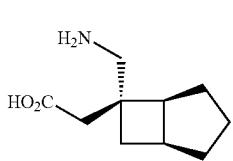
(XIV)

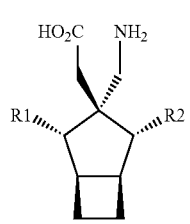
(XV)

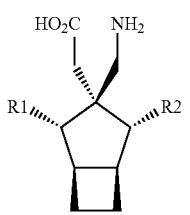
(XVI)

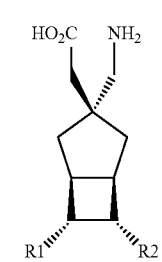
(XVII)

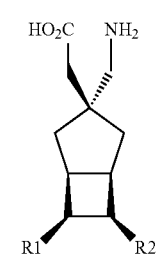
(XVIII)

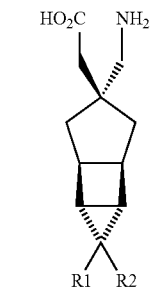
(XIX)

-continued

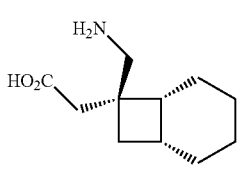
XX

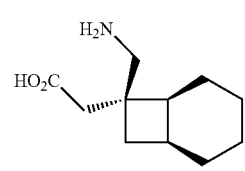
XXI

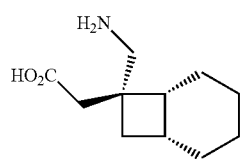
XXII

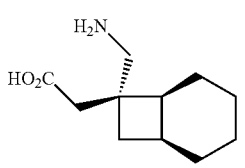
XXIII

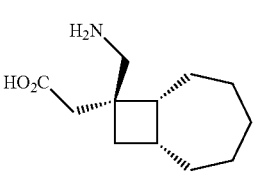
XXIV

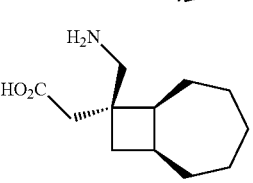
XXV

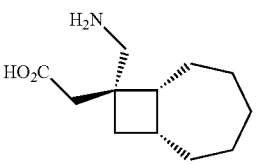
XXVI

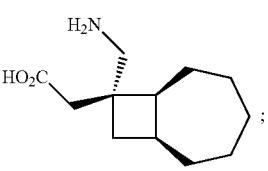
XXVII

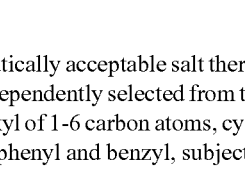
;

or a pharmaceutically acceptable salt thereof, wherein $R^1$ and $R^2$ are each independently selected from the group H, straight or branched alkyl of 1-6 carbon atoms, cycloalkyl of from 3-6 carbon atoms, phenyl and benzyl, subject to the proviso that, except in the case of a tricyclooctane compound of formula (XIX), $R^1$ and $R^2$ are not simultaneously hydrogen.

5. The method according to claim 1 where the alpha-2-delta ligand is:

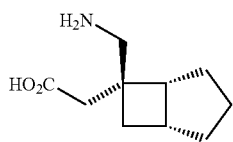

(XI)

or a pharmaceutically acceptable salt thereof.

6. The method according to claim 1 where the alpha-2-delta ligand is [(1R,5R,6S)-6-(Aminomethyl)bicyclo[3.2.0]hept-6-yl]acetic acid or (2S,4S)-4-(3-Chloro-phenoxy)-pyrrolidine-2-carboxylic acid, or a pharmaceutically acceptable salt thereof.

7. The method according to claim 1 where the alpha-2-delta ligand is [(1R,5R,6S)-6-(Aminomethyl)bicyclo[3.2.0]hept-6-yl]acetic acid or a pharmaceutically acceptable salt thereof.

8. The method as claimed in any one of claims 1-3, where administration is on an as needed basis.

9. The method as recited in claim 1 wherein the alpha-2-ligand has a binding affinity of less than 100 nM.

10. The method as recited in claim 8 wherein the alpha-2-ligand has a binding affinity of less than 100 nM.

11. The method as recited in claim 1 wherein the alpha-2-ligand has a binding affinity of less than 50 nM.

12. The method as recited in claim 8 wherein the alpha-2-ligand has a binding affinity of less than 50 nM.

* * * * *